United States Patent [19]

Sawicki et al.

[11] Patent Number: 4,579,675
[45] Date of Patent: Apr. 1, 1986

[54] N-SUBSTITUTED ENAMINONES AND OLEAGINOUS COMPOSITIONS CONTAINING SAME

[75] Inventors: Robert A. Sawicki; Benjamin J. Kaufman, both of Wappingers Falls, N.Y.; Phillip B. Valkovich, Spring, Tex.; Joseph B. Biasotti, Lagrangeville, N.Y.

[73] Assignee: Texaco Inc., White Plains, N.Y.

[21] Appl. No.: 550,156

[22] Filed: Nov. 9, 1983

[51] Int. Cl.$^4$ .......................... C10M 1/20; C10M 1/32
[52] U.S. Cl. ........................... 252/51.5 A; 252/51.5 R; 548/545; 548/546
[58] Field of Search ..................... 252/51.5 A, 51.5 R; 548/545, 546

[56] References Cited

U.S. PATENT DOCUMENTS

| | | | |
|---|---|---|---|
| 3,280,034 | 10/1966 | Anzenberger et al. | 252/51.5 A |
| 3,647,691 | 3/1972 | Vineyard | 252/51.5 A |
| 4,247,404 | 1/1981 | Shields | 252/51.5 A |

FOREIGN PATENT DOCUMENTS 985373 3/1965 United Kingdom .......... 252/51.5 A

Primary Examiner—Mrs. Y. Harris-Smith
Attorney, Agent, or Firm—Robert A. Kulason; James J. O'Loughlin

[57] ABSTRACT

Described are novel enaminones of the formula:

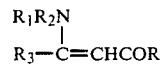

wherein R is a lower alkyl or oxyalkyl group having 1 to 5 carbon atoms, $R_1$ is an alkyl group having from 1 to 200 carbon atoms or a similar alkyl group substituted by nitrogen, oxygen or other inert substituents; $R_2$ is hydrogen or an alkyl group having from 1 to 20 carbon atoms; $R_3$ is an alkyl or substituted alkyl group having from 1 to 20 carbon atoms. These products are prepared by the reaction of a 1,3-dicarbonyl compound and a primary or secondary amine analog.

In neat or mixed form, the present compounds are useful as dispersants-detergents in oleaginous compositions.

2 Claims, No Drawings

N-SUBSTITUTED ENAMINONES AND OLEAGINOUS COMPOSITIONS CONTAINING SAME

FIELD OF THE INVENTION

This invention is directed to novel enaminones prepared by reacting 1,3-dicarboxy compounds with primary or secondary amines. More specifically, the invention is directed to the use of such compounds as dispersants and detergents in oleaginous compositions.

Enaminones are compounds containing the chemical functionality $N-C=C-C=O$ and are most commonly prepared by the reaction of a primary or secondary amine with a $\beta$-dicarbonyl compound. Vinylogous amides result from the reaction of an amine with a 1,3-diketone while 3-keto esters react with amines to yield vinylogous urethanes. Compounds of this class previously have not been suggested for use in oleaginous compositions including hydrocarbon fuels and lubricants.

BACKGROUND OF THE INVENTION

The literature evidences little activity as regards this class of compounds. However one patent of interest is U.S. Pat. No. 2,840,600 which discloses N-substituted trimethylene diamine-N'alkanoic acids as corrosion inhibitors in fuel oils. British Pat. No. 776,121 describes surface active esters acid salts of $\beta$-aminobutyric acid containing substituents on the nitrogen atom and prepared by reacting ethyl acetoacetate with a primary amine and hydrogenating the product. The *J. Indian Chemical Society* 7,669-76 (1930) relates the condensation of ethyl acetoacetate with aromatic amines, to give various substituted anilides of unstated properties. *Chemical Abs.*, Vol. 26, 2178$^c$(1932) describes condensation products of benzylamine with acetoacetic ester. *J. Chemical Society* (1935) 1568-70 discloses the interaction of aromatic diamines with ethyl acetoacetate. *J. Chemical Society* (1956) 2597-600 describes the condensation of acetylacetone with 1,2-diamines to form diazepines.

SUMMARY OF THE INVENTION

In a product aspect, the invention resides in novel N-substituted enaminones of the formula:

$$R_3-\underset{\underset{R_1R_2N}{|}}{C}=CHCOR$$

wherein R is a lower alkyl or oxyalkyl group having 1 to 5 carbon atoms; $R_1$ is an alkyl group having 1 to 200 carbon atoms or a similar alkyl group substituted by nitrogen, oxygen or other inert substituent; $R_2$ is hydrogen or an alkyl group having 1 to 20 carbon atoms; and $R_3$ is an alkyl or substituted alkyl group having 1 to 20 carbon atoms.

These compounds can be readily prepared by reacting a 1,3-dicarbonyl compound and a primary or secondary amine under an inert atmosphere in a solvent, optionally in the presence of an acid catalyst, such as p-toluenesulfonic acid and the like.

The reaction proceeds as follows:

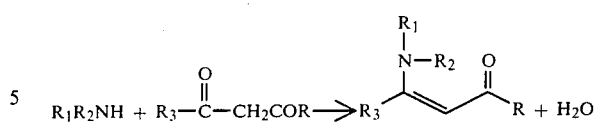

Preferred $R_1$ groups are:

$R_5NHCH_2CH_2-CH_2-$; and

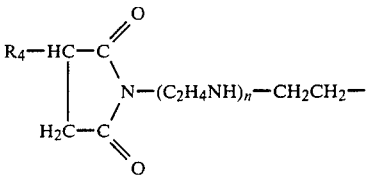

$R_4$ is hydrogen or a $C_1-C_{100}$ alkyl or alkenyl group; $R_5$ is hydrogen or a $C_1-C_{20}$ alkyl or alkenyl group and n ranges from 1 to 6.

In a compositional aspect, the invention resides in an oleaginous composition containing a major amount of a hydrocarbon and a minor detergent-dispersant amount of at least one of the above compounds.

The above invention is further illustrated by the following examples.

A. Preparation of Amine Containing Succinimides

The succinimides described below were prepared from a polyisobutenyl succinic acid anhydride with an average molecular weight of 1400 and a saponification number of approximately 53.

EXAMPLE I

This example illustrates the reaction of ethylenediamine and polyisobutenyl succinic acid anhydride.

Into a 3 liter 4-neck flask fitted with a mechanical stirrer, Dean-Stark trap with condenser, thermometer and thermoregulator was added 1000 g. of polyisobutenyl succinic acid anhydride and 500 ml. toluene. Ethylenediamine (100 g., 1.67 mol.) was added over 15 min. with the pot temperature rising to 44° C. After complete addition, the reaction mixture was heated at reflux for 3 hours (100° C.). The stopcock on the Dean-Stark trap was then closed and the solution heated an additional 30 min. at 130 ° C. collecting 28.5 mol. of an EDA water mixture. The Dean-Stark trap was removed, the flask was fitted with a simple distillation apparatus and the toluene solvent was removed by distillation (1 hr., 130° C., water aspirator vacuum). The reaction mixture was allowed to cool and 500 ml. heptane was added. The product was filtered through filter aid and stripped on a rotary evaporator at 95° C. under water aspirator vacuum. The product (975 g.) had a percent nitrogen (%N) composition of 1.3 and a total base number (TBN) of 25.

EXAMPLE II

This example illustrates the reaction of diethylenetriamine (DETA) and polyisobutenyl succinic acid anhydride.

Polyisobutenyl succinic anhydride (500 g.) and diethylenetriamine (73 g., 0.71 mol) was added to a 1 liter 4-neck flask equipped as in Example I. The reaction mixture was heated 2 hours at 140° C. The Dean-Stark trap was removed and a distillation apparatus set up. The solution was subsequently heated for 1 hour at 160° C. at water aspirator vacuum. After cooling, heptane (300 ml.) was added and after complete mixing the product was filtered through filter aid. Stripping for 1 hour at 95° C. under water aspirator vacuum afforded 475 g. of a product having a %N of 2.3 and a TBN of 55.

EXAMPLE III

B. PREPARATION OF ENAMINONE DERIVATIVES

Into a 500 ml. 4-neck flask fitted with a thermometer, Dean-Stark trap with condenser, thermoregulator and mechanical stirrer was added 100 g. Example I, 4.5 g. (45 mmol). 2,4-pentanedione, 100 ml. toluene and 0.9 g. (4.7 mmol.) p-toluenesulfonic acid monohydrate. The mixture was heated for 5 hours at 110° C. The flask was then fitted with a distillation apparatus and the toluene stripped at 120° C. for 15 min. The mixture was cooled to room temperature and 100 ml. heptane added. After filtering the product was stripped at 95° C. for 1 hour at water aspirator vacuum to afford 92 g. of a material with 1.1% N composition. The infrared shows additional peaks at 1580 and 1620 cm.$^{-1}$, relative to the starting succinimide.

EXAMPLE IV

This example illustrates the reaction of the product from Example I with ethyl acetoacetate.

The procedure used was identical to that of Example III except that 5.8 g. (45 mmol.) ethyl acetoacetate was substituted for the 2,4-pentanedione and the crude product after filtration was washed twice with 50 ml. methanol. Stripping yielded 64 g. of a product containing 1.1% N and a new IR band at 1620 cm$^{-1}$.

EXAMPLE V

This example illustrates the reaction of the product from Example II with ethyl acetoacetate.

The product from Example II (100 g.), 14.2 (0.11 mol.) ethyl acetoacetate, 100 ml. toluene and 2 g. (0.01 mol.) p-toluenesulfonic acid monohydrate was placed in a 500 mol. 4-neck flask equipped as Example III. The mixture was heated 4½ hours at 110° C. The toluene solvent was then distilled off at 110° C. under water aspirator vacuum and after cooling 125 ml. heptane was added. After filtering the crude product was washed twice with 50 ml. methanol and stripped in the usual way. The product (95 g.) contained 1.7% N and had an additional IR band at 1570 cm$^{-1}$.

EXAMPLE VI

This example illustrates the reaction of a succinimide prepared from triethylene tetramine (DETA) and polyisobutenyl succinic acid anhydride with ethyl acetoacetate.

The succinimide (as a 50% concentrate in diluent oil) employed in this reaction had a 0.88% N and a TBN of 25. Into a 500 ml. 4-neck flask fitted as in Example III was added 100 g. of the succinimide described above, 2 g. (15.4 mmol.) ethyl acetoacetate and 100 ml. toluene. The mixture was heated 4½ hours at 110° C. The toluene was distilled off for 1 hour at 100° C. and 45 mins. at 130° C. The product was filtered hot affording 60 g. of a material containing 0.75% N and a TBN of 17. Additional peaks appeared in the IR at 1600 cm$^{-1}$.

Table I below illustrates the performance of the compounds of the foregoing Example and how these are more effective as dispersants than the starting nitrogenous compounds.

TABLE

BENCH VC TEST RESULTS

| Additive | Wt. %[1] | % Turbidity |
|---|---|---|
| Example I | 4 | 36.5 |
| (EDA Succinimide) | 6 | 18.0 |
| Example III | 4 | 43.5 |
| (2-4 Pentanedione Enaminone of example I) | 6 | 25.0 |
| Example IV | 4 | 42.5 |
| (Ethyl acetoacetate Enaminone of example I) | 6 | 23.5 |
| Example II | 4 | 31.5 |
| (DETA Succinimide) | 6 | 8.5 |
| Example V | 4 | 26.5 |
| (Ethyl acetoacetate Enaminone of example II) | 6 | 6.0 |
| TETA Succinimide | 4 | 36.0 |
|  | 6 | 10.5 |
| Example VI | 4 | 26.5 |
| (Ethyl acetoacetate Enaminone of TETA Succinimide) | 6 | 3.5 |

[1] as 50% concentrates

The Bench VC test is described in U.S. Pat. No. 4,248,719. The above data show less turbidity indicating greater dispersant power for the final products.

EXAMPLE VII

This Example shows in preparation of the enamine ester of N-1-(oleyl)-1,3-diaminopropane and ethyl acetoacetate.

To "Duomeen OL" (175 g) and xylene (200 ml) was added ethyl acetoacetate (65 g). The mixture was refluxed until water (10.1 ml) was azeotroped over. The xylene was then removed by vacuum evaporation. Analysis of the product gave:

%N=6.6
TBN=190.7
MWt=387

This product was evaluated as follows:

| (A) Chevrolet Carburetor Detergency Test - Phase III | |
|---|---|
| PTB | Δ % |
| 20 | +25 v. commercial detergent @ 20 PTB |

This result shows improved detergency for the present compound:

| (B) Buick Detergency Test | |
|---|---|
| Additive Dosage | Carburetor Rating |
| 2.5 PARTS per 1000 barrels | 7.1 |
| 3.8 PARTS per 1000 barrels | 8.0 |
| 5.0 PARTS per 1000 barrels | 8.2 |

10 = Clean
1 = Dirty

The Chevrolet Carburetor Detergency test is described in U.S. Pat. No. 4,177,041. The Buick Detergency Test is described in U.S. Pat. No. 4,204,841.

The compounds of the invention are blended in an oleaginous composition including oils and fuels in an amount ranging from 0.001 to 10% on the basis of the weight of such compositions.

Such fuels and oils will naturally also contain other conventional additives in an amount sufficient to achieve each additive's function.

What is claimed is:

1. An enaminone reaction product prepared by reacting ethylacetoacetate with an alkenylsuccinimide in the presence of p-toluene sulfonic acid; said alkenylsuccinimide providing an alkenylsuccinyl moiety represented by the formula

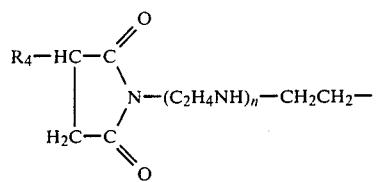

in which $R_4$ is hydrogen or a $C_1$–$C_{100}$ alkyl or alkenyl group and n ranges from 1 to 6.

2. An oleaginous lubricating oil composition comprising a major amount of a hydrocarbon and an effective detergent-dispersant amount of the reaction product of claim 1.

* * * * *